(12) United States Patent
Stutterheim et al.

(10) Patent No.: US 10,770,607 B2
(45) Date of Patent: Sep. 8, 2020

(54) INTERCONNECTED PHOTOVOLTAIC MODULE CONFIGURATION

(71) Applicant: FLISOM AG, Niederhasli (CH)

(72) Inventors: Stephan Stutterheim, Wallisellen (CH); Andreas Bogli, Vogelsang (CH); Ivan Sinicco, Altendorf (CH)

(73) Assignee: FLISOM AG, Niederhasli (CH)

( * ) Notice: Subject to any disclaimer, the term of this patent is extended or adjusted under 35 U.S.C. 154(b) by 0 days.

(21) Appl. No.: 16/067,086

(22) PCT Filed: Jan. 4, 2017

(86) PCT No.: PCT/IB2017/000005
§ 371 (c)(1),
(2) Date: Jun. 28, 2018

(87) PCT Pub. No.: WO2017/118904
PCT Pub. Date: Jul. 13, 2017

(65) Prior Publication Data
US 2019/0027625 A1    Jan. 24, 2019

Related U.S. Application Data

(60) Provisional application No. 62/275,585, filed on Jan. 6, 2016.

(51) Int. Cl.
*H01L 31/046*    (2014.01)
*H01L 31/0749*    (2012.01)
(Continued)

(52) U.S. Cl.
CPC ........ *H01L 31/046* (2014.12); *A61B 1/00135* (2013.01); *A61B 1/126* (2013.01);
(Continued)

(58) Field of Classification Search
None
See application file for complete search history.

(56) References Cited

U.S. PATENT DOCUMENTS

2014/0305494 A1    10/2014    Dhir

FOREIGN PATENT DOCUMENTS

DE    10109643 A1    9/2002

OTHER PUBLICATIONS

Machine Translation Kessler DE 1019643—Accessed Oct. 25, 2019 (Year: 2002).*

(Continued)

*Primary Examiner* — Shannon M Gardner
(74) *Attorney, Agent, or Firm* — Patterson & Sheridan, LLP

(57) ABSTRACT

Embodiments of the present disclosure generally relate to an apparatus and method of forming a photovoltaic module assembly that contains a plurality of interconnected photovoltaic modules that are used to generate an amount of power when exposed to electromagnetic radiation. The formed photovoltaic module assembly will generally include two or more photovoltaic modules that can generate and deliver power to an external grid, external network or external device. The photovoltaic module assembly can be a stand alone power generating device or be disposed within an array of interconnected photovoltaic devices.

20 Claims, 9 Drawing Sheets

(51) Int. Cl.
*H01L 31/18* (2006.01)
*H02S 40/36* (2014.01)
*H01L 31/042* (2014.01)
*A61B 90/70* (2016.01)
*A61B 1/00* (2006.01)
*A61B 1/12* (2006.01)
*H01L 31/0392* (2006.01)
*G02B 23/24* (2006.01)

(52) U.S. Cl.
CPC ........ *A61B 90/70* (2016.02); *H01L 31/03926* (2013.01); *H01L 31/042* (2013.01); *H01L 31/0749* (2013.01); *H01L 31/18* (2013.01); *H02S 40/36* (2014.12); *A61B 1/00142* (2013.01); *G02B 23/2476* (2013.01); *Y02E 10/541* (2013.01)

(56) References Cited

OTHER PUBLICATIONS

International Search Report and Written Opinion for PCT/IB2017/000005, dated Mar. 27, 2017.

\* cited by examiner

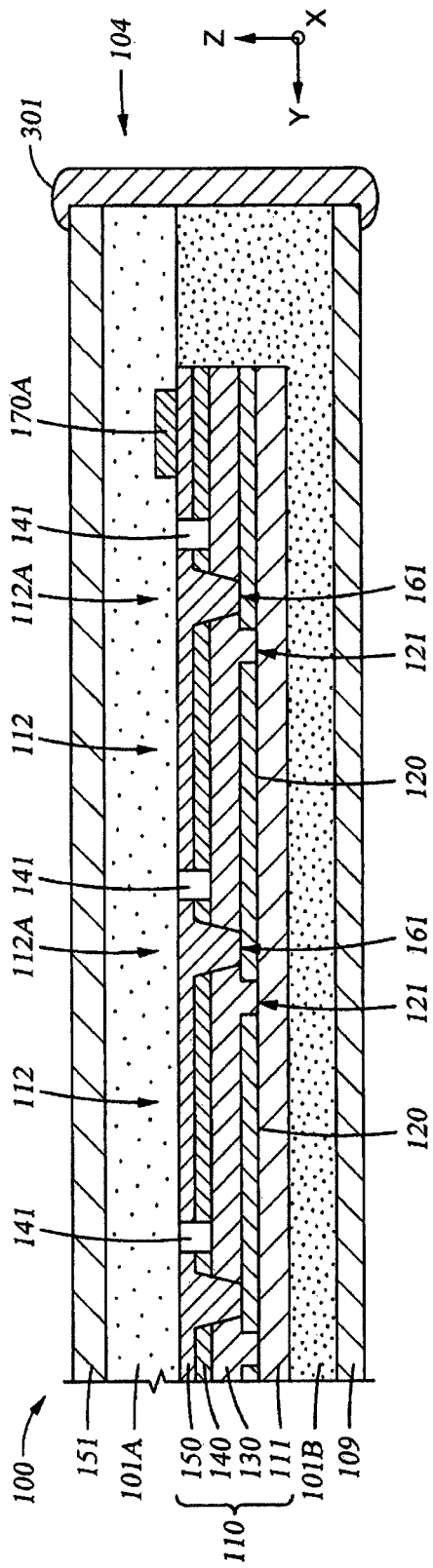
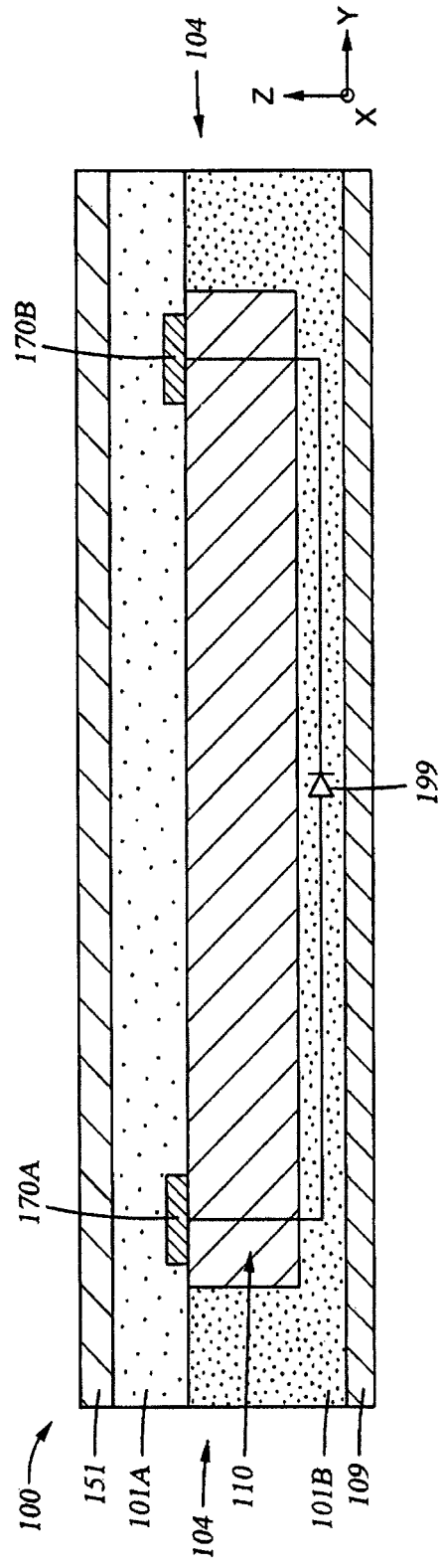

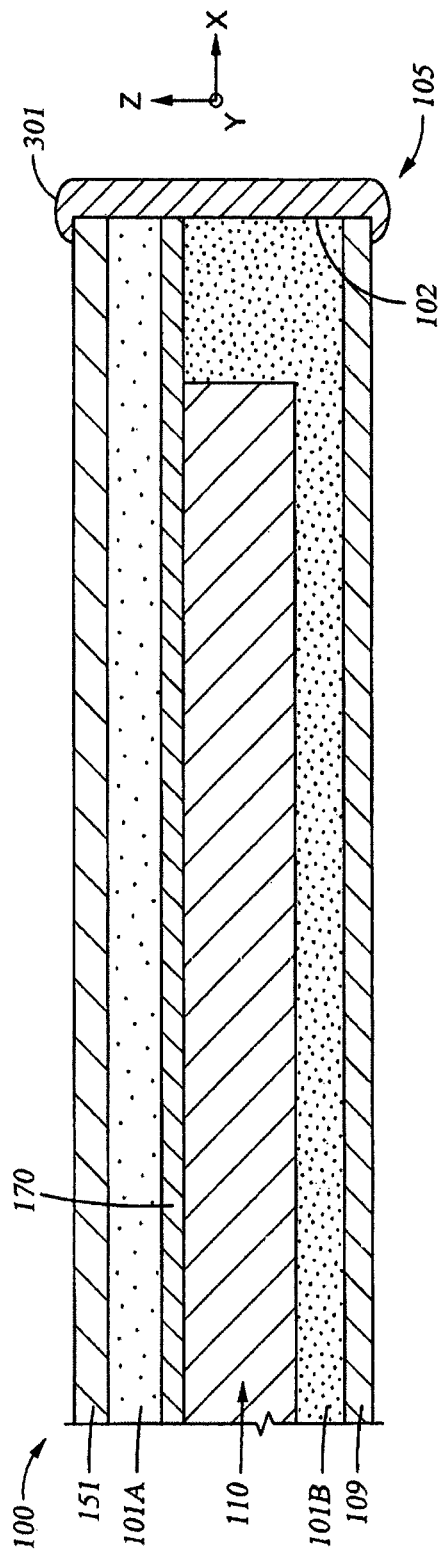
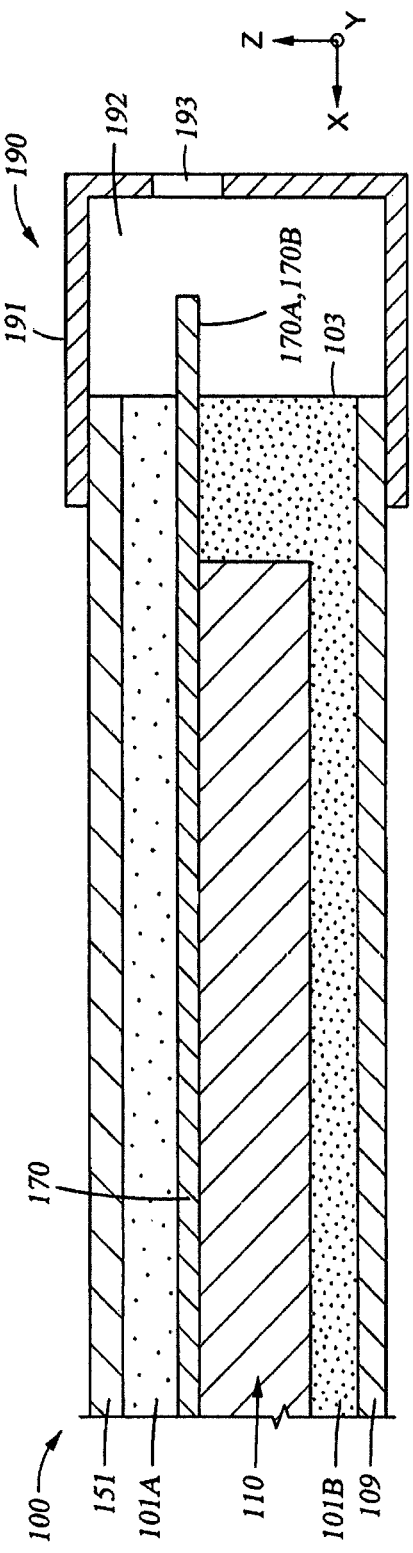
Fig. 2A
Fig. 2B

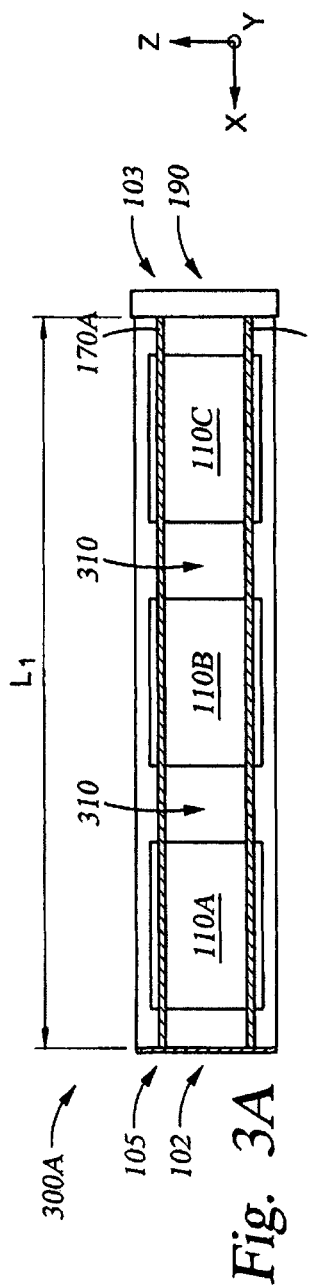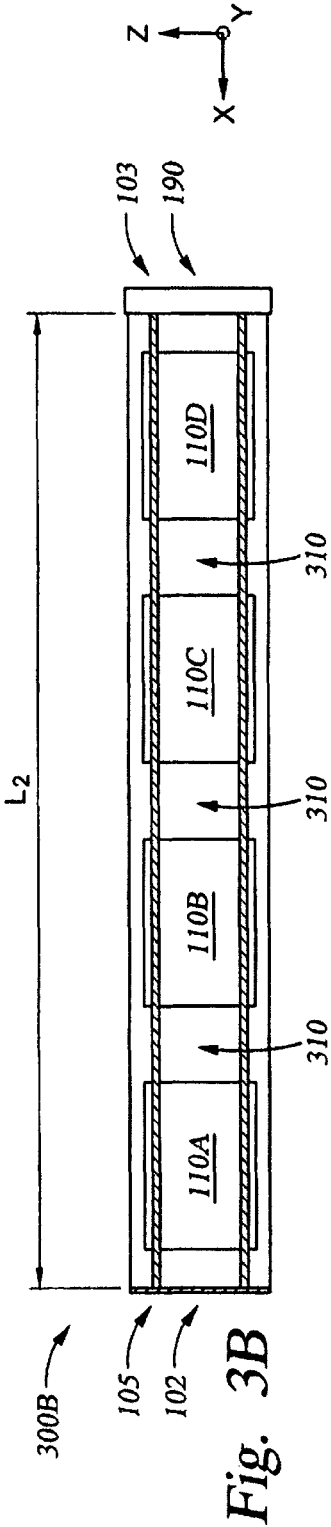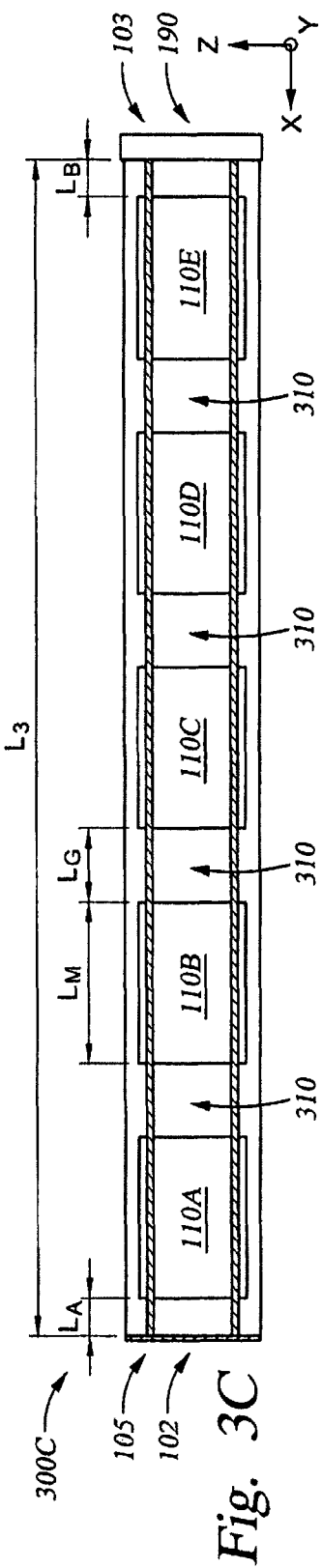

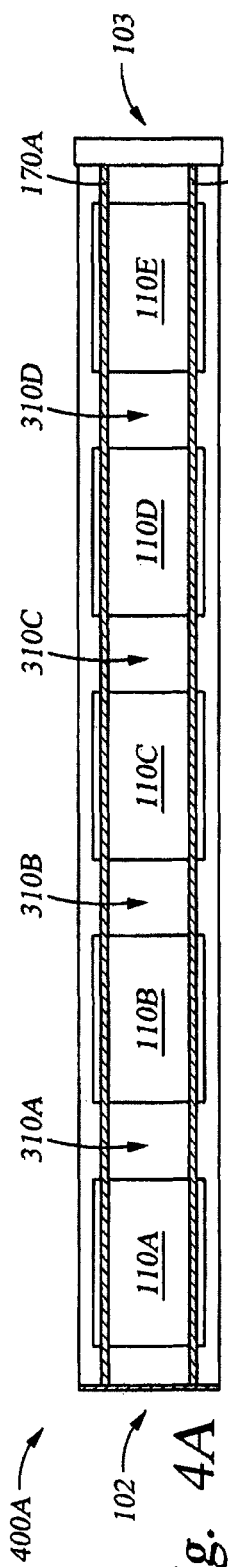
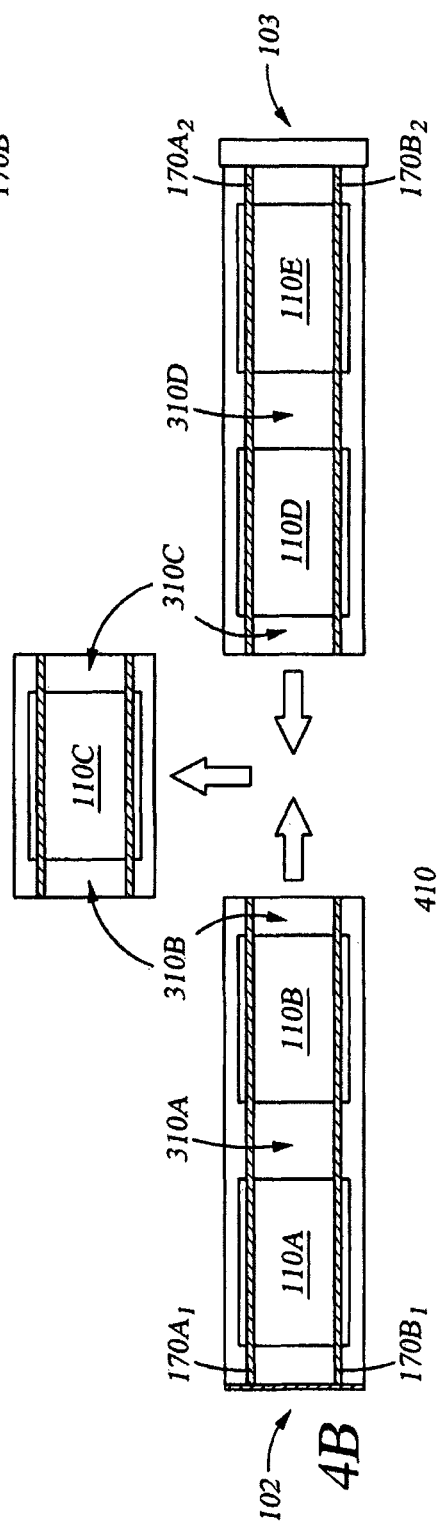
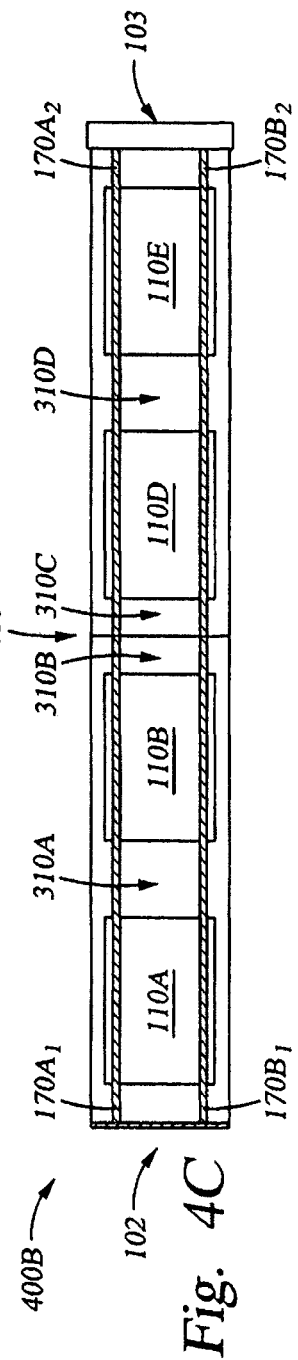
Fig. 4A
Fig. 4B
Fig. 4C

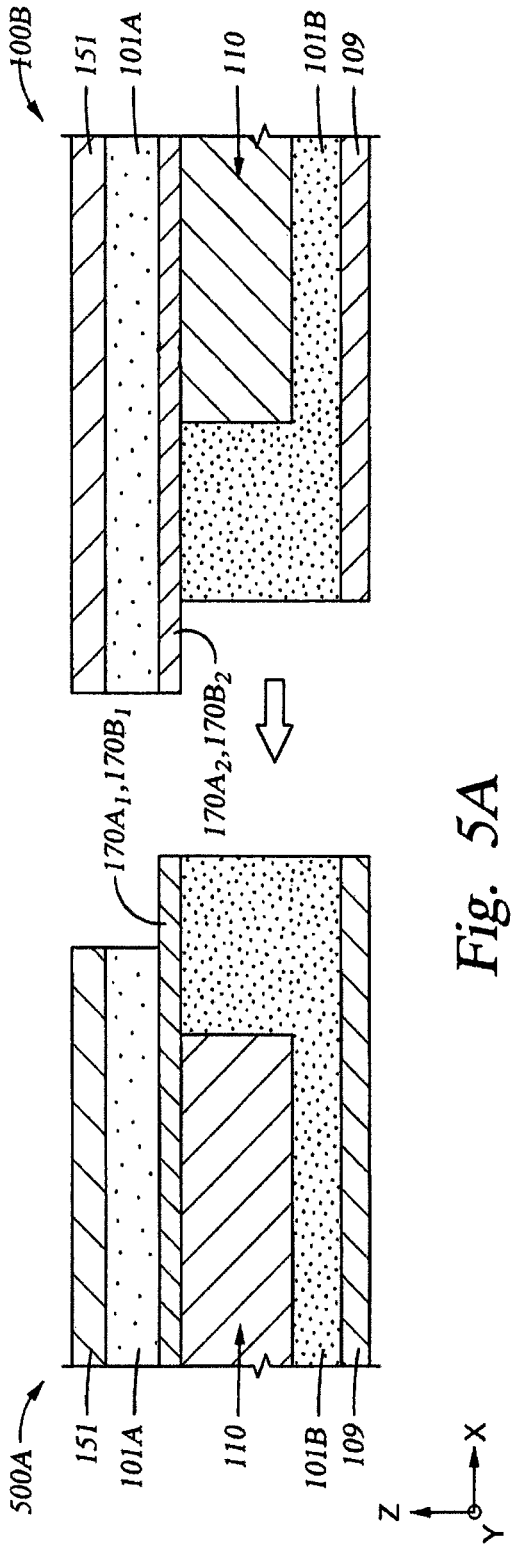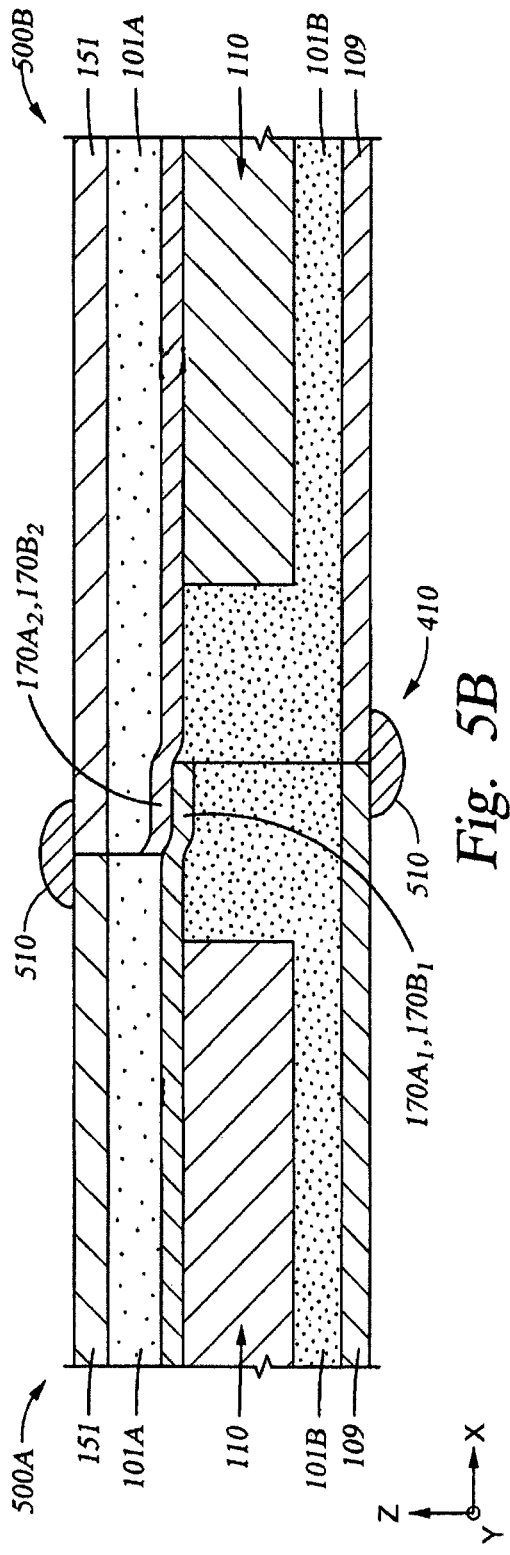

INTERCONNECTED PHOTOVOLTAIC MODULE CONFIGURATION

CROSS-REFERENCE TO RELATED APPLICATIONS

This application is a continuation of International Application No. PCT/IB2017/000005, filed Jan. 4, 2017, which is a continuation of U.S. Application No. 62/275,585, filed Jan. 6, 2016. The above applications are all incorporated by reference herein.

BACKGROUND

Field

Embodiments of the present disclosure generally relate to an apparatus and method of forming an interconnected photovoltaic module device.

Description of the Related Art

Photovoltaic devices generally include one or more photovoltaic modules that include arrays of interconnected photovoltaic cells. Photovoltaic modules can be classified according to the materials which are used in the photovoltaic cells. Thin-film photovoltaic cells are an alternative design to the traditional crystalline silicon-based design for photovoltaic cells. Examples of thin-film photovoltaic cells include solar cells including at least one thin-film absorber layer. The thin-film absorber layer may, for example, comprise one layer of amorphous silicon, cadmium telluride (CdTe), and copper indium gallium selenide (CIGS). Thin-film photovoltaic modules are generally composed of a number of electrically interconnected optoelectronic components, such as photovoltaic cells. Thin-film-photovoltaic cells are generally composed of a stack of three material layers: (1) a conducting back-contact electrode layer, (2) a semiconductive photovoltaic material layer, also known as the absorber, and (3) a conducting front-contact electrode layer, where the front-contact layer is usually transparent.

One advantage available when making thin-film photovoltaic devices is the option of using monolithic integration, which is the interconnection of several optoelectronic components on a single substrate. Monolithic integration includes a sequence of layer deposition and scribing steps to form the individual photovoltaic cells. Photovoltaic cells based on thin-film semiconductive materials, such as CIGS or CdTe, show promise for less expensive solar electricity, lower energy payback time, a greater range of applications, and improved life-cycle impact as compared to traditional wafer-based silicon photovoltaic devices or solar cells. Compared to wafer-based photovoltaic devices, thin-film monolithic photovoltaic modules may have lower production costs due to reduced material quantities required to form thin film solar cells, reduced labor costs, and ease of automatic production of large quantities of photovoltaic modules, such as using roll-to-roll manufacturing techniques.

Another advantage available when making thin-film photovoltaic devices is the option of making the devices flexible. Flexible thin-film photovoltaic devices may be formed by encapsulating a flexible photovoltaic module component within layers of polymer and other materials to form a larger photovoltaic module assembly that includes multiple photovoltaic modules. Flexible thin-film photovoltaic devices have many desirable applications that are not available to most conventional crystalline silicon wafer type solar cells or glass substrate thin-film photovoltaic applications. For example, flexible solar cells may be used in building integrated photovoltaic (BIPV) applications and/or on clothing, flexible canopies, or other non-rigid supporting member type applications. In various commercial BIPV applications, the length of the formed photovoltaic module assemblies often need to be customized to meet the BIPV application's power requirements and/or form an aesthetically pleasing array of photovoltaic module assemblies. Such BIPV type photovoltaic module assemblies might be produced in lengths of up to 20 meters, and generate high output voltages.

However, flexible photovoltaic devices are ordinarily thinner than glass-encapsulated photovoltaic devices and may be subject to greater stresses and strains due to flexing during installation and/or normal use, which may cause damage to the encapsulated electrical and photovoltaic module components. Due to stress and strain induced in a formed photovoltaic module, and normal production yield issues, one or more of the photovoltaic modules within a formed photovoltaic module assembly can become damaged and/or inoperable, which can render the whole photovoltaic module assembly unusable. Therefore there is a need for a photovoltaic module assembly that can be reworked to make it functional again to avoid having to scrap the whole photovoltaic module assembly when one of many photovoltaic modules becomes inoperable.

Therefore, there is a need for an apparatus and method of forming a cost effective and reliable thin-film photovoltaic device that solves the problems described above.

SUMMARY

Embodiments of the disclosure may provide a flexible photovoltaic apparatus, comprising a front sheet, a back sheet, an array of photovoltaic modules disposed between the front sheet and the back sheet, a first busbar that is aligned in the first direction, and is electrically coupled to the cathode region of each sub-module in each photovoltaic module, and a second busbar that is aligned in the first direction, and is electrically coupled to the anode region of each sub-module. The array of photovoltaic modules include a gap that is formed in a first direction between adjacent edges of adjacent photovoltaic modules disposed within the array. Each photovoltaic module will also include two or more sub-modules that each have a cathode region and an anode region, and wherein the anode region is disposed at an opposite end of the photovoltaic module from the cathode region.

Embodiments of the disclosure may further provide a method of forming a photovoltaic module, comprising disposing an array of photovoltaic modules on a first adhesive layer that is disposed over a back sheet, disposing a portion of a first busbar over the cathode region of each sub-module, wherein the first busbar is aligned in the first direction, disposing a portion of a second busbar over the anode region of each sub-module, wherein the second busbar is aligned in the first direction, disposing a second adhesive layer over the first busbar, the second busbar, the array of photovoltaic modules, the first adhesive layer and the back sheet, disposing a front sheet over the second adhesive layer, and laminating the front sheet, the second adhesive layer, the first busbar, the second busbar, the array of photovoltaic modules, the first adhesive layer and the back sheet to encapsulate the photovoltaic modules. The array of photovoltaic modules include a gap that is formed in a first direction between adjacent edges of adjacent photovoltaic modules disposed within the array. Each photovoltaic module will also include two or more sub-modules that each have a cathode region and an anode region, and wherein the anode region is disposed at an opposite end of the photovoltaic module from the cathode region.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 1B is a side sectional view of a portion of a photovoltaic module disposed within the photovoltaic module assembly illustrated in FIG. 1A, according to an embodiment of the disclosure.

FIG. 1C is a side sectional view of another portion of a photovoltaic module disposed within the photovoltaic module assembly illustrated in FIG. 1A, according to an embodiment of the disclosure.

FIG. 2A is a side sectional view of an end of the photovoltaic module assembly illustrated in FIG. 1A, according to one embodiment of the disclosure.

FIG. 2B is a side sectional view of an end of the photovoltaic module assembly illustrated in FIG. 1A, according to one embodiment of the disclosure.

FIGS. 3A-3C are top views of different configurations of photovoltaic module assemblies, according to embodiments of the disclosure.

FIG. 4A is a top view of a photovoltaic module assembly, according to an embodiment of the disclosure.

FIG. 4B is a top view of the photovoltaic module assembly illustrated in FIG. 4A that has a damaged photovoltaic module removed therefrom, according to an embodiment of the disclosure.

FIG. 4C is a top view of a reconfigured version of the photovoltaic module assembly illustrated in FIG. 4A, according to an embodiment of the disclosure.

FIG. 5A is a side sectional view of two reworked portions of a photovoltaic module assembly, according to an embodiment of the disclosure.

FIG. 5B is a side sectional view of the two reworked portions of the photovoltaic module assembly, which is illustrated in FIG. 5A, in an electrically connected configuration, according to an embodiment of the disclosure.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments of the present disclosure generally relate to an apparatus and method of forming a photovoltaic module assembly that contains a plurality of interconnected photovoltaic modules that are used to generate a desired amount of power when exposed to electromagnetic radiation. The formed photovoltaic module assembly will generally include two or more photovoltaic modules that can generate and deliver power to an external grid, external network or external device. The photovoltaic module assembly can be a stand alone power generating device or be disposed within an array of interconnected photovoltaic devices.

Figure 1A:
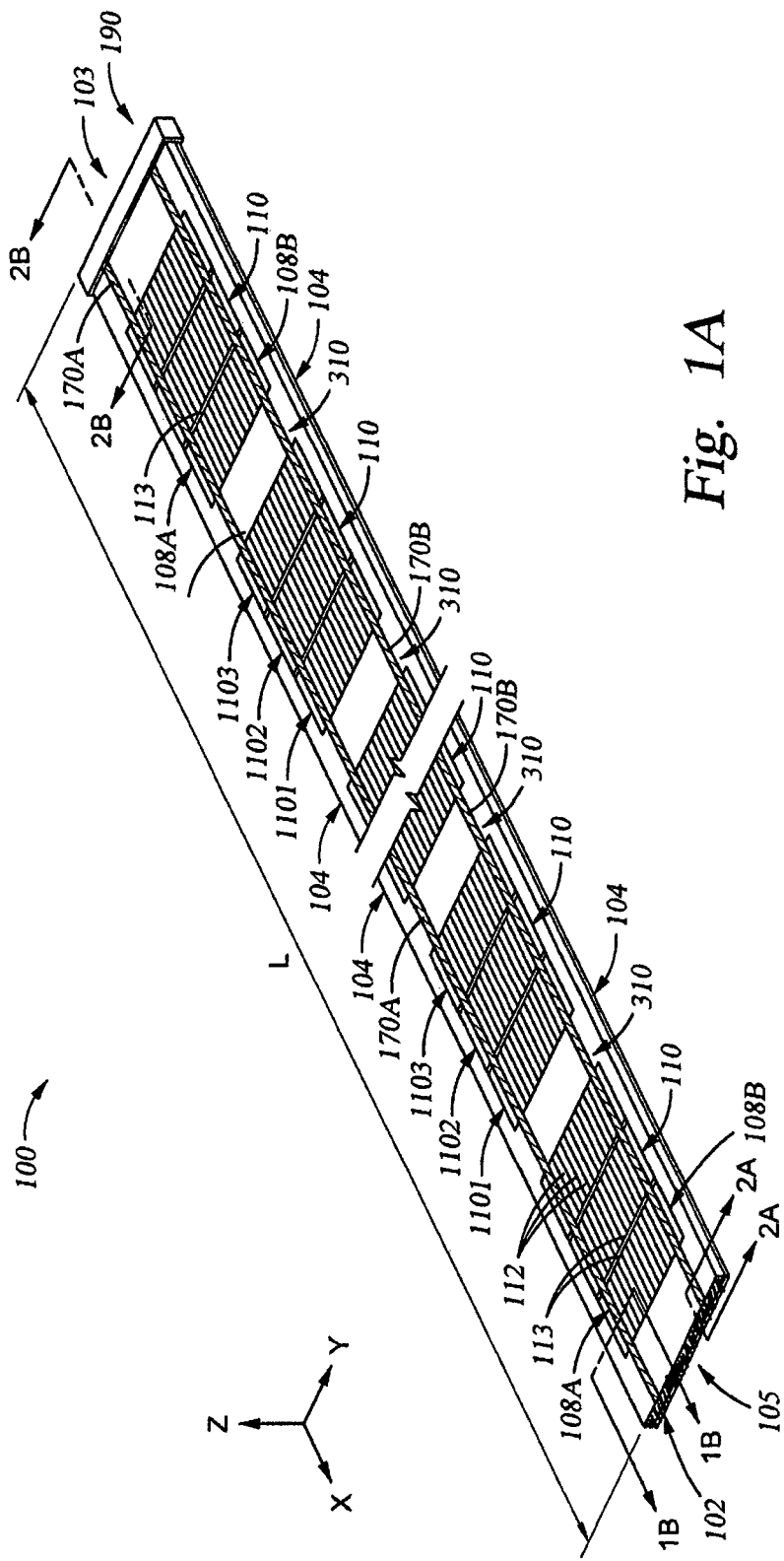
FIG. 1A is an isometric view of a photovoltaic module assembly, according to one embodiment of the disclosure.

FIG. 1A is an isometric view of a photovoltaic module assembly 100, according to one embodiment of the disclosure. The photovoltaic module assembly 100 may include multiple optoelectronic devices, such as photovoltaic devices (e.g., solar cells), diodes, and LEDs. In some embodiments, the photovoltaic module assembly 100 includes two or more photovoltaic modules 110 that are interconnected by a plurality of busbars 170, such as busbars 170A and 170B. The busbars 170A and 170B are disposed in a spaced apart relationship along the length L of the photovoltaic module assembly 100. The interconnected photovoltaic modules 110 and busbars 170 are encapsulated to protect these current generating and/or current carrying electrical components from the external environment during normal use. Each photovoltaic module 110 includes one or more photovoltaic sub-modules, such as the photovoltaic sub-modules 1101, 1102, and 1103 illustrated in FIG. 1A. In one example, a photovoltaic module 110 includes two or more photovoltaic sub-modules, which are hereafter referred to as sub-modules, such as three to five sub-modules.

In some embodiments, the sub-modules are monolithically formed on a substrate by use of multiple photovoltaic device forming steps. FIG. 1B is a side sectional view of a portion of the sub-module 1101 of the first photovoltaic module 110 disposed within the photovoltaic module assembly 100 shown in FIG. 1A. In some embodiments, the sub-modules within each photovoltaic module 110 are formed on a substrate 111. The substrate 111 may be a flexible substrate, a rigid substrate, or semi-rigid material containing substrate (e.g., semi-rigid substrates distort under their own weight, but are unable to be formed in a roll form), and is typically formed from an electrically insulating material. In one example, a flexible substrate material may be used to form the substrate 111, such as a substrate formed from a polyimide material. In one example, the polyimide substrate has a thickness in the Z-direction from about 5 micrometers (μm) to about 200 μm, such as from about 15 μm to about 100 μm.

In some embodiments, each sub-module within each photovoltaic module 110 may include a plurality of thin-film layers that are deposited on the substrate 111, and then patterned (e.g., scribed) to form a plurality of monolithically interconnected photovoltaic cells 112 that are electrically connected in series. In other embodiments, the sub-modules can include a photovoltaic device formed on another substrate that is then positioned on the substrate 111.

A sub-module can include, for example, a back-contact layer 120 formed on the substrate 111, an absorber layer 130 formed over the back-contact layer 120, and a front-contact layer 150 formed over the absorber layer 130. The back-contact layer 120 can be fabricated from a material having a high optical reflectance and is commonly made of molybdenum (Mo) although several other thin-film materials, such as metal chalcogenides, molybdenum chalcogenides, molybdenum selenides (such as $MoSe_2$), sodium (Na)-doped Mo, potassium (K)-doped Mo, Na- and K-doped Mo, transition metal chalcogenides, tin-doped indium oxide (ITO), doped or non-doped indium oxides, doped or non-doped zinc oxides, zirconium nitrides, tin oxides, titanium nitrides, titanium (Ti), tungsten (W), tantalum (Ta), gold (Au), silver (Ag), copper (Cu), and niobium (Nb) may also be used or included advantageously. In some embodiments, the back-contact layer 120 is deposited onto the substrate 111 by use of sputtering process.

The absorber layer 130 is typically made of an "ABC" material, wherein "A" represents elements in group 11 of the periodic table of chemical elements as defined by the International Union of Pure and Applied Chemistry including copper (Cu) or silver (Ag), "B" represents elements in group 13 of the periodic table including indium (In), gallium (Ga), or aluminum (Al), and "C" represents elements in group 16 of the periodic table including sulfur (S), selenium (Se) or tellurium (Te). An example of an ABC material is the $Cu(In,Ga)Se_2$ semiconductor also known as CIGS. In some embodiments, the absorber layer may include a polycrystalline material. In other embodiments, the absorber layer may be a monocrystalline material. Another example of a material that may be used as the absorber layer is chalcopyrite.

The front-contact layer 150 can be an electrically conductive and optically transparent material, such as a transparent conductive oxide (TCO) layer. For example, in some embodiments, the front-contact layer 150 may be formed of doped or non-doped variations of materials, such as indium oxides, tin oxides, or zinc oxides.

In some embodiments, a semiconductive buffer layer 140 can be disposed between the absorber layer 130 and the front-contact layer 150. The semiconductive buffer layer 140 ordinarily has an energy bandgap higher than 1.5 eV. The semiconductive buffer layer may be formed of materials, such as CdS, Cd(S,OH), CdZnS, indium sulfides, zinc sulfides, gallium selenides, indium selenides, compounds of (indium, gallium)-sulfur, compounds of (indium, gallium)-selenium, tin oxides, zinc oxides, Zn(Mg,O)S, Zn(O,S) material, or variations thereof.

FIGS. 1A and 1B illustrate photovoltaic modules 110 that each include three sub-modules 1101, 1102 and 1103 that contain an array of photovoltaic cells 112 that extends in the Y-direction from a first end region 108A to a second end region 108B within the photovoltaic module 110. As shown in FIG. 1B, the photovoltaic cells 112 are spaced apart in the Y-direction and consecutive photovoltaic cells (e.g., adjacent photovoltaic cells 112) are interconnected to each other by a plurality of serial interconnects 112A (i.e., also referred to as P1, P2 and P3 scribe lines), that extend in the X-direction. The layers of each photovoltaic cell 112, such as layers 120-150, are formed in a stacked orientation in the Z-direction (the third direction). The photovoltaic cells 112 in each sub-module (e.g., sub-module 1102) are also isolated from other photovoltaic cells 112 disposed in adjacent sub-modules (e.g., sub-modules 1101 and 1103) by use of one or more isolation scribe lines 113 that are aligned in the Y-direction, and are used to separate the sub-modules. The photovoltaic cells 112 are electrically connected in series between busbars 170A and 170B by use of the formed serial interconnects 112A.

The serial interconnect 112A forms an electrical connection between each consecutive photovoltaic cell 112 in the array of cells. Each serial interconnect 112A includes a connecting groove 161 (i.e., the P2 scribe line) that is formed through the front-contact layer 150, the semiconductive buffer layer 140 and the absorber layer 130 to form an electrically conductive path that electrically serially connects consecutive photovoltaic cells in the array. The conductive path may be formed by melting a portion of the absorber layer 130 during a laser scribing process used to form the connecting groove 161. For example, one connecting groove 161 electrically connects the front-contact layer 150 of the third photovoltaic cell 112 to the back-contact layer 120 of the fourth photovoltaic cell 112.

In some embodiments, each serial interconnect 112A includes a pair of grooves to electrically isolate portions of each adjacent photovoltaic cell. A back-contact groove 121 (i.e., the P1 scribe line) electrically isolates the back-contact layers 120 of adjacent photovoltaic cells 112 from each other. A front-contact groove 141 (i.e., the P3 scribe line) electrically isolates the front-contact layers 150 of adjacent photovoltaic cells from each other. The serial interconnects 112A can thus be used to electrically connect the photovoltaic cells 112 in series.

Referring back to FIG. 1A, in some embodiments, photovoltaic module assembly 100 includes two or more busbars 170, such as busbars 170A and 170B, that are used to interconnect the photovoltaic modules 110 disposed within the photovoltaic module assembly 100. The power generated by the photovoltaic cells 112 in the sub-modules within each photovoltaic module 110 is collected by the two or more busbars and delivered to an external power connection (not shown) that is formed within a junction box 190 disposed at one end of the photovoltaic module assembly 100. As noted above, each photovoltaic module 110 disposed within the photovoltaic module assembly 100 may be selected (e.g., binned) so that the output of all of the photovoltaic modules 110 in the photovoltaic module assembly 100 have similar performance characteristics to assure that the overall output of the photovoltaic module assembly 100 can be optimized. The photovoltaic module assembly performance characteristics may be determined by use of an analysis process that measures a performance characteristic of sub-modules, such as conversion efficiency (CE), photocurrent (I), series resistance ($R_s$), fill factor (FF), sheet resistance (ρ), open circuit voltage ($V_{oc}$), dark current ($I_{dc}$), short circuit current ($I_{sc}$), quantum efficiency (QE), maximum power ($P_{max}$), maximum current ($I_{max}$), maximum voltage ($V_{max}$) and/or spectral response.

In some embodiments, the photovoltaic module assembly 100 is configured such that the photovoltaic modules 110 in the photovoltaic module assembly 100 are electrically connected in parallel, such that, for example, when exposed to light the cathodic end of the sub-modules within all of the photovoltaic modules 110 are connected together by the first busbar 170A and the anodic end of the submodules in all of the photovoltaic modules 110 are connected together by the second busbar 170B. The cathodic end may be associated with the first end region 108A and the anodic end is associated with the second end region 108B. In this case, the series connected photovoltaic cells 112 within each sub-module generate a voltage difference between the first busbar 170A and the second busbar 170B during normal operation. In one example, each sub-module includes a plurality of photovoltaic cells 112 that form a voltage between about 0.5 volts and about 1000 volts between the busbars 170A and 170B and a current of between 100 milliamps (mA) and 4000 mA during normal operation. However, in some embodiments, it may alternately be desirable to connect the photovoltaic modules 110 in series, such that the voltage generated by the sub-modules in the photovoltaic modules 110 adds along the length L (FIG. 1A) of the photovoltaic module assembly 100.

In general, the busbars 170 may be formed from a variety of materials including metals, such as copper, nickel plated copper, silver plated copper, tin plated copper, steel, stainless steel, or other commonly used conductors. The busbars 170 can have a width in the Y-direction (FIG. 1A) that is from about 100 μm to about 3 centimeters (cm), such as from about 2 millimeters (mm) to about 8 mm, such as from about 3 mm to about 5 mm. Furthermore, the busbars 170 can have a thickness in the Z-direction from about 0.05 mm to about 2 mm, such as from about 0.1 mm to about 1 mm, such as from about 0.15 mm to about 0.3 mm.

Each of the busbars 170 is in electrical communication with a portion of each of the sub-modules in a photovoltaic module. In one example, the first busbar 170A is electrically coupled to a portion of the back-contact layer 120 at a first end (e.g., end region 108A) of the submodules through a connection region formed between the front-contact layer 150 and the back-contact layer 120. Similarly, in this example, the second busbar 170B may be electrically coupled to a portion of the front-contact layer 150 disposed at an opposing end (e.g., end region 108B) of each of the sub-modules. In some embodiments, regions of the busbars 170A and 170B are bonded to their respective portion of the sub-modules by use of a bonding material, such as a conductive adhesive, solder material or other similar material, and/or a bonding process (e.g., thermal bonding, ultrasonic bonding) that is used to form an electrical contact between a portion of the busbars and the conductive portions of the sub-modules.

As noted above, the photovoltaic modules 110 and busbars 170 are encapsulated within the photovoltaic module assembly 100 by use of a front-side adhesive 101A and a back-side adhesive 101B. In some embodiments, the front-side adhesive 101A and the back-side adhesive 101B completely surround and encapsulate each of the photovoltaic modules 110 and busbars 170. In one example, the front-side adhesive 101A is formed over the front-contact layer 150 of each of the sub-modules, and also over the first and second busbars 170A and 170B. The front-side adhesive 101A may be formed of a flexible material, such as a flexible polymer. For example, in one embodiment the front-side adhesive 101A may be formed from EVA, a thermoplastic olefin (TPO) based polymer or a TPO blend.

The back-side adhesive 101B is disposed over the side of the substrate 111 that is opposite to the side that the sub-module(s) is formed on. The back-side adhesive 101B may be formed of a flexible material, such as a flexible polymer. For example, in one embodiment the back-side adhesive 101B may be formed from EVA, a thermoplastic olefin-based polymer (TPO) or a TPO polymer blend. The back-side adhesive 101B may contact the front-side adhesive 101A at each of the ends of the photovoltaic modules and also on the sides of the photovoltaic modules, so that the front-side adhesive 101A and the back-side adhesive 101B completely surround and encapsulate the photovoltaic modules.

A front sheet 151 can be disposed on an outer surface of the front-side adhesive 101A, such as a top surface of the front-side adhesive 101A. The front sheet 151 can be formed of a transparent material, such as a transparent thermoplastic polymer. In some embodiments, the front sheet 151 may be formed of a flexible material. In some embodiments, a flexible front sheet 151 may have a thickness in the Z-direction from about 0.005 mm to about 1 mm. However, in some embodiments, the front sheet 151 may be formed of a rigid material or semi-rigid material.

A back sheet 109 can be disposed on an outer surface of the back-side adhesive 101B, such as a bottom surface of the back-side adhesive 101B. The back sheet 109 may include a reflective material, such as a metal layer, a reflective polymer or a polymer with a reflective layer (e.g., metal foil) formed over a first surface that is adjacent to the bottom surface of the back-side adhesive 101B. In some embodiments, the back sheet 109 may be formed from a flexible material (e.g., flexible polymer layer and/or flexible metal foil). In some embodiments, the back sheet 109 may include a fiber-reinforced polymer material. In some embodiments, a flexible back sheet 109 may have a thickness in the Z-direction from about 0.005 mm to about 3 mm. However, in some embodiments, the back sheet 109 may be formed of a rigid or semi-rigid material.

In some embodiments, as schematically illustrated in FIG. 10, the photovoltaic module assembly 100 may include one or more bypass diodes 199 that are designed to prevent the effects of hot-spot heating. The bypass diode 199 is integrated within the encapsulated portion of the photovoltaic module assembly 100 during manufacturing and is connected in parallel, but with an opposite polarity to the sub-modules as shown in FIG. 1C. In some configurations, the leads of a bypass diode 199 are electrically connected to the first and second busbars 170A and 170B by use of a bonding technique, such as a soldering technique.

The photovoltaic module assembly 100 may also include an insulation end seal 105 that is disposed at one end of the photovoltaic module assembly 100, as illustrated in FIG. 2A. The insulation end seal 105 may include a portion of the edge seal 301 that is disposed over the end 102 of the photovoltaic module assembly 100. The presence of the edge seal 301 at the end 102 can be used to assure that the first and second busbars 170A and 170B that typically extend to the end 102 of the photovoltaic module assembly 100 are not exposed to the external environment. In some configurations, the edge seal 301 may also be disposed on one or both sides 104 of the formed photovoltaic module assembly 100, as illustrated in FIG. 1B. The presence of the edge seal 301 at the end 102 and sides 104 of the photovoltaic module assembly 100 can be used to assure that photovoltaic module assembly 100 will meet electrical certification requirements and eliminate common photovoltaic apparatus manufacturing and photovoltaic device failure modes. In general, the edge seal 301 comprises a polymeric material, such as an elastomer, for example a butyl rubber that can be formed by dispensing a liquid precursor material along the edge of the photovoltaic module assembly 100 and allowing it to cure. The edge seal 301 can be formed of a material having a low water vapor transmission rate (WVTR), such as WVTR less than about $1 \times 10^{-4}$ (g/m$^2$·day). The edge seal 301 may also be protected by a "clamp" or termination box that is disposed over a portion of the front sheet 151 and the back sheet 109 along one or more of the ends and/or edges of the photovoltaic module assembly 100. The "clamp" or termination box may be made out of a rigid material like a thermoplastic material.

The photovoltaic module assembly 100 may further include a junction box 190 that is disposed at one end of the photovoltaic module assembly 100, as illustrated in FIG. 2B. The junction box 190 may include a region 192 that allows the portions of the busbars 170 disposed at the end 103 of the photovoltaic module assembly 100 to be electrically connected to one or more external devices, such as, for example, electronics used to charge one or more external batteries. In some configurations, one or more walls 191 of the junction box 190 may be positioned over the end 103 of the photovoltaic module assembly 100 to sealably enclose a region 192. The first and second busbars 170A and 170B may extend into the junction box 190 past the end 103 of the photovoltaic module assembly 100 to allow for an electrical connection to be made to the busbars within the region 192 of the junction box 190. In some configurations, the walls 191 of the junction box 190 may be adhesively bonded to the surface of the back sheet 109, the sides 104 of the photovoltaic module assembly 100 and a surface of the front sheet 151 by use of an adhesive and/or potting material to form an environmental seal therebetween. The junction box 190 may include one or more connectors for connecting the first busbars 170A and 170B with one or more external conductors (not shown) that are disposed through a sealable opening 193 of the junction box 190.

Figure 1D:
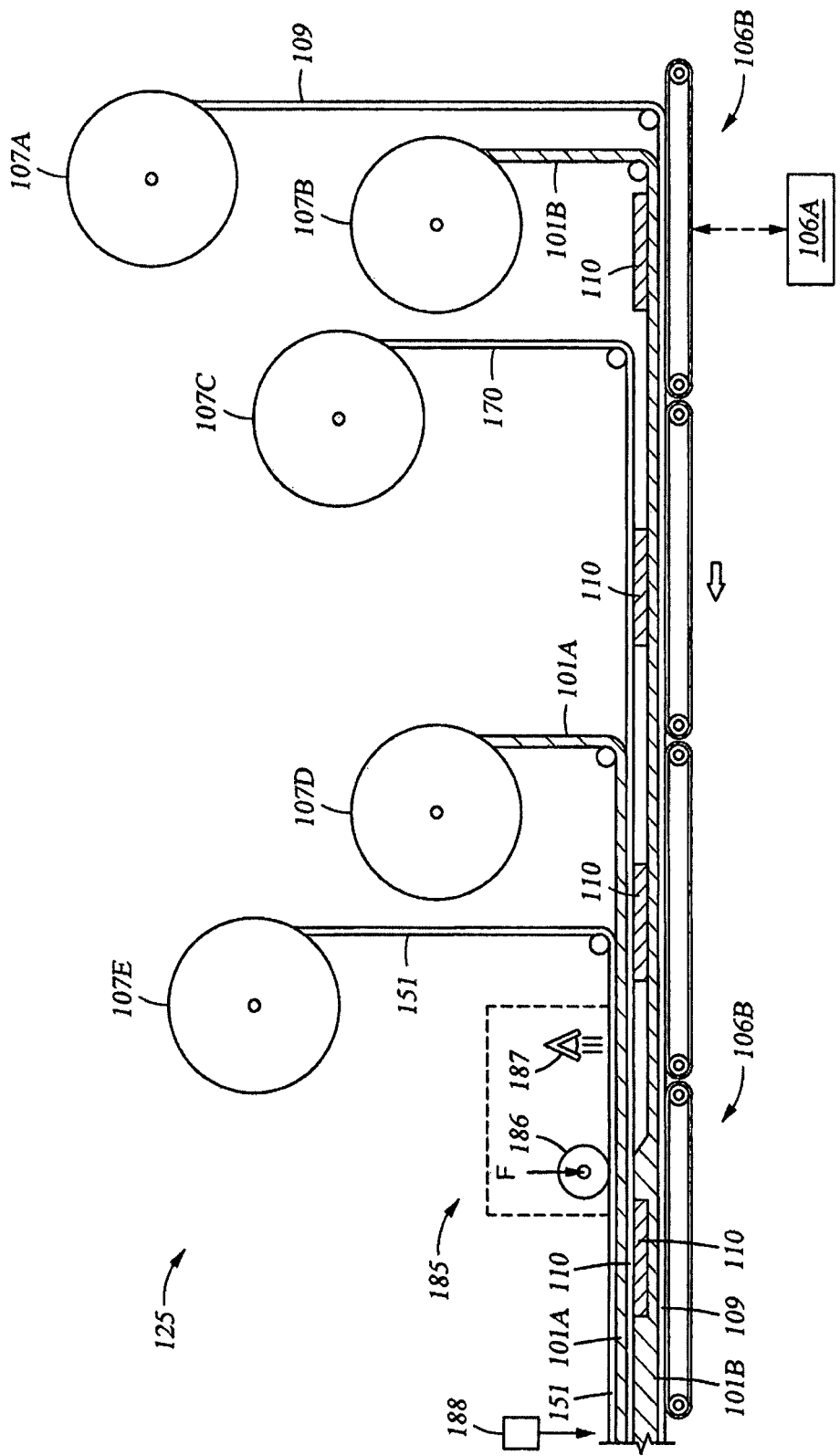
FIG. 1D is a schematic view of a photovoltaic module assembly forming apparatus, according to an embodiment of the disclosure.

FIG. 1D is a schematic view of an apparatus 125 that may be used to form a photovoltaic module assembly described herein. The apparatus 125 illustrated in FIG. 1D is not intended to be limiting as to the scope of the disclosure provided herein, but is intended to schematically illustrate an apparatus that may be used to form a photovoltaic module assembly, such as the photovoltaic module assembly 100 illustrated in FIG. 1A, by use of an automated or semi-automated process sequence. The apparatus 125 may include a back-sheet roll 107A, a back-side adhesive layer roll 107B, two or more busbar rolls 107C, an front-side adhesive layer roll 107D, a front-sheet roll 107E, material guiding rollers, a controller 106A and a conveyor system 106B. The controller 106A and conveyor system 106B are configured to help control the transportation of portions of the various materials contained in the rolls 107A-107E to form a photovoltaic module assembly using an automated or semi-automated process sequence. In some configurations, the controller 106A may include a central processing unit (CPU) (not shown), memory (not shown), and support circuits (or I/O) (not shown). The CPU may be one of any form of computer processors that are used in industrial settings for controlling various system processes and hardware (e.g., conveyors, dispensing devices, robotics, etc.) and monitor the system and related transport processes (e.g., sub-module position, detector signals, etc.). The memory is connected to the CPU, and may be one or more of a readily available memory, such as flash memory, random access memory (RAM), read only memory (ROM), floppy disk, hard disk, or any other form of non-volatile digital storage, local or remote. Software instructions and data can be coded and stored within the memory for instructing the CPU. The support circuits are also connected to the CPU for supporting the processor in a conventional manner. A program (or computer instructions) readable by the controller 106A determines which tasks and/or processes are performable in the apparatus 125.

The photovoltaic module assembly formation process sequence performed by the apparatus 125 may first include individually placing the tested and sorted photovoltaic modules 110, with the thin-film layer side facing up, on a portion of back-side adhesive layer 101B that is disposed over a portion of the back sheet 109. The portions of the back-side adhesive layer 101B and the back sheet 109 on which the photovoltaic modules 110 are placed are delivered or rolled out from their respective rolls 107B and 107A.

Two or more busbars 170, which are spaced apart in the Y direction, are then dispensed from the two or more busbar rolls 107C (only one shown) over a surface of each of the photovoltaic modules 110. The two or more busbars can be disposed over the end regions 108A and 108B of the photovoltaic modules 110 in this step as the conveyor system 106 moves the photovoltaic modules 110, back-side adhesive layer 101B and the back sheet 109 in the +X-direction.

Next, a portion of the front-side adhesive layer 101A is then disposed over the busbars 170, photovoltaic module 110, back-side adhesive layer 101B and portion of the back sheet 109, by use of the controller 106A, conveyor system 106B and front-side adhesive layer roll 107D.

Next, a portion of the front-sheet 151 is then disposed over the front-side adhesive layer 101A, busbars 170, photovoltaic module 110, back-side adhesive layer 101B and portion of the back sheet 109, by use of the conveyor system 106 and front-sheet layer roll 107E.

The layers used to form the photovoltaic module assembly 100 are then laminated together to form at least part of one or more encapsulated photovoltaic module assemblies. The lamination process may be performed in a lamination module 185. The lamination process will typically include the delivery of heat, such as radiant heat from a lamp 187, and the application of pressure. In some embodiments, pressure may be applied to the various module assembly layers by applying a controlled force F using an actuator (not shown) and roller 186. The photovoltaic module assemblies 100 having a desirable length can then be sectioned from the continuous encapsulated photovoltaic module containing roll created by the apparatus 125. Two formed photovoltaic module assemblies 100 that are disposed within the encapsulated photovoltaic module containing roll can be separated from each other at an interconnection region 310 (FIGS. 3A-3C) formed between the last photovoltaic module in one photovoltaic module assembly and the first photovoltaic module in a second photovoltaic module assembly. Details of the interconnection region and sectioning process are discussed in greater detail below. Alternately, the lamination process may be performed in a batch process that includes sectioning the photovoltaic module assemblies 100 from the continuous encapsulated photovoltaic module containing roll created by the apparatus 125 at a formed interconnection region 310, and then placing multiple sectioned photovoltaic module assemblies in a pressure and heat applying device (e.g., autoclave).

Finally, the process sequence may end with the edge seal(s) 301 and junction box(es) 190 being attached to each of the laminated photovoltaic module assemblies. In some embodiments, the materials used to form the edge seal(s) 301 and bond the junction box(es) to the laminated photovoltaic module assembly may be dispensed from a device 188 disposed downstream of the lamination module 185.

Photovoltaic Module Assembly Configuration Examples

FIGS. 3A, 3B and 3C illustrate examples of various photovoltaic module assembly configurations, such as the photovoltaic module assemblies 300A, 300B and 300C that each include three, four or five photovoltaic modules and have a length $L_1$, $L_2$ and $L_3$, respectively. One will appreciate that the configurations of the photovoltaic module assemblies shown in FIGS. 3A-3C are not intended to be limiting as to the scope of the disclosure provided herein, since a photovoltaic module assembly may contain any number of photovoltaic modules to achieve a desired power output. Thus, in some cases a photovoltaic module assembly may contain at least two photovoltaic modules, such as between about two and about twenty five photovoltaic modules.

As shown in FIGS. 3A, 3B and 3C, each photovoltaic module assembly contains a plurality of interconnected photovoltaic modules 110 that are disposed in an array and spaced apart by an interconnection region 310, which is also referred to herein as a gap, that is formed during the photovoltaic module assembly formation process. The interconnection region 310 is generally defined as an encapsulated region formed between adjacent photovoltaic modules 110 through which the busbars 170 extend so as to interconnect two adjacently positioned photovoltaic modules 110. The busbars 170 are oriented such that they extend in a first direction (i.e., X-direction) and are spaced apart a fixed distance in a second direction (i.e., Y-direction) across the length L of the photovoltaic module assembly. The fixed and regular orientation of the busbars 170 allows photovoltaic module assemblies to be easily interconnected with other similarly formed photovoltaic module assemblies, and also allows components within a photovoltaic module assembly to be easily replaced should one of the components (e.g., photovoltaic modules) disposed therein become damaged during manufacturing or use in the field, as will be discussed further detail below.

In general, the photovoltaic module assemblies shown in FIGS. 3A, 3B and 3C contain the same components as the photovoltaic module assembly 100 discussed above. However, the photovoltaic module assemblies 300A, 300B and 300C each have a different number of interconnected photovoltaic modules 110 so that a desired amount of power can be generated by each photovoltaic module assembly. In some embodiments, each of the photovoltaic modules 110 and formed interconnection regions 310 are formed such that they have a consistent fixed size so that multiple photovoltaic module assemblies can be easily positioned in a desired regular array or pattern across a roof, façade or other type of supporting element on which the power generating photovoltaic module assemblies are disposed. Typically, the spacing in the X-direction between the edge of the substrate 111 in the photovoltaic module closest to the end 102 (e.g., photovoltaic module 110A in FIG. 3C) and the end 102, and the spacing in the X-direction between the edge of the substrate 111 in the photovoltaic module closest to the end 103 (e.g., photovoltaic module 110C in FIG. 3C) and the end 103, or also referred to herein as the end lengths $L_A$ and $L_B$ respectively, are each formed to a fixed or consistent size across similarly formed photovoltaic module assemblies.

In some embodiments, depending on the number of photovoltaic modules 110 and the size of the interconnection regions 310 each photovoltaic module assembly will have a formed photovoltaic module assembly length L that is set by the number of photovoltaic modules disposed in the formed photovoltaic module assembly. In one example, the photovoltaic module assembly 300C (FIG. 3C) includes five photovoltaic modules 110A-110E that each have the same module length $L_M$, or distance edge-to-edge of a substrate 111 in the X-direction, end lengths $L_A$ and $L_B$, and four formed interconnection regions 310 that each have the same gap length $L_G$, or distance between the adjacently disposed edges of the substrates 111 in adjacent photovoltaic modules in the X-direction, to achieve a photovoltaic module assembly length $L_3$. In some embodiments, the formed photovoltaic module assembly length L can be determined by use of the equation:

$$L = L_A + L_B + N(L_M) + (N-1)(L_G),$$

where N is equal to the number of photovoltaic modules. Typically, the module length $L_M$ is set by the electrical requirements of the photovoltaic module assembly, the gap length $L_G$ may be between about 0.5 cm and about 10 cm, the end length $L_A$ may be between about 0.5 cm and about 5 cm, and end length $L_B$ may be between about 0.5 cm and about 5 cm. In one example, the photovoltaic module assembly length L may be greater than about 0.5 meters (m). In one example, the photovoltaic module assembly length L may be about 10 m, 20 m, 40 m or greater.

Figure 3D:
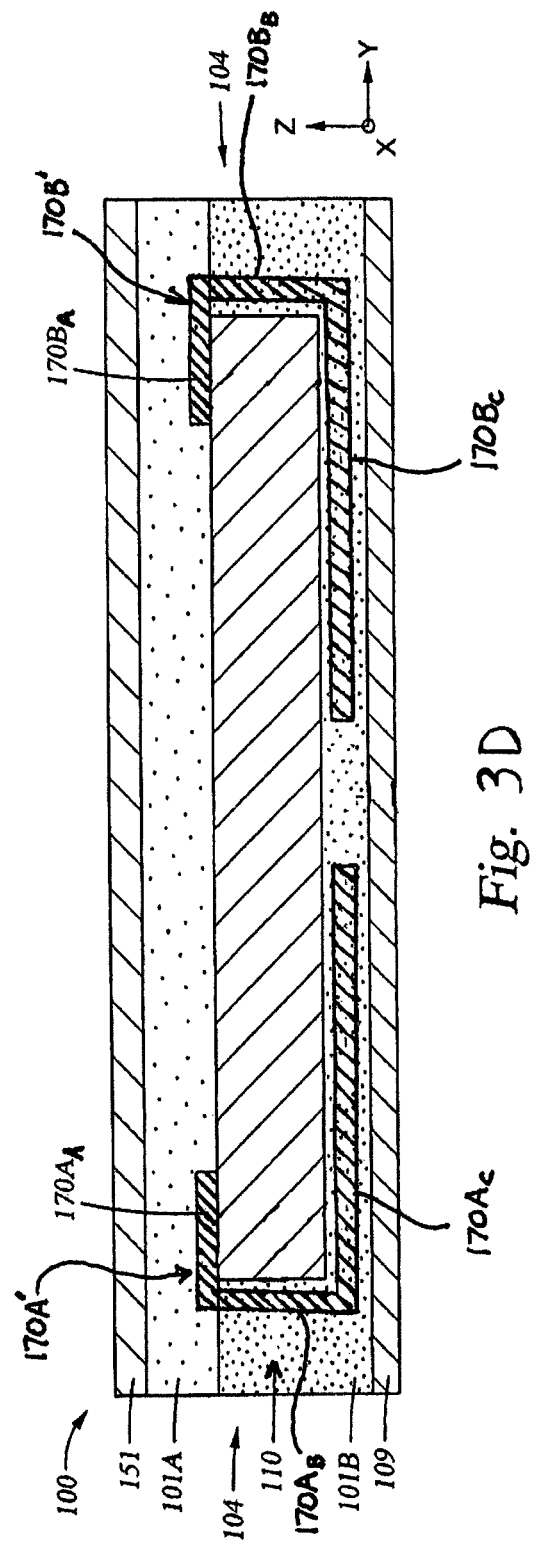
FIG. 3D is a side sectional view of a portion of a photovoltaic module disposed within a photovoltaic module assembly, according to an embodiment of the disclosure.

In some embodiments, in which the photovoltaic module assembly length L is an extended distance, such as lengths greater than 10 meters, the cross-sectional area of the busbars 170 may need to be increased to reduce its electrical resistance and increase its current carrying capacity across the extended length L of the busbars 170. Thus, it is believed that by increasing the cross-sectional area of each of the busbars 170 in an extended length photovoltaic module assembly the power generated by photovoltaic modules positioned at one end (e.g., end 102) of the photovoltaic module assembly can be efficiently transferred to an opposing end (e.g., end 103), on which the junction box is positioned. However, due to the desire to form photovoltaic module assemblies that are flexible, allow the photovoltaic module assemblies to be formed by a roll-to-roll process, prevent the larger cross-section busbars from encroaching the light receiving surfaces of the photovoltaic modules 110, and/or not dramatically increase the overall width (e.g., Y-direction) of the formed photovoltaic module assemblies, the major current carrying regions $170A_C$, $170B_C$ of larger cross-section busbars 170A', 170B' may be disposed underneath each of the photovoltaic modules 110, as shown in FIG. 3D. In this configuration, each of the larger cross-section busbars 170A', 170B' include a connection region $170A_A$, $170B_A$, an interconnection region $170A_B$, $170B_B$ and current carrying regions $170A_C$, $170B_C$, respectively. In general, the connection regions $170A_A$, $170B_A$ are formed such that they primarily contact the end regions 108A, 108B of the photovoltaic modules 110, and the interconnection region $170A_B$, $170B_B$ is formed to interconnect the connection region $170A_A$, $170B_A$ with the current carrying region $170A_C$, $170B_C$. In some embodiments, the connection region $170A_A$, $170B_A$ and interconnection region $170A_B$, $170B_B$ include a plurality of thin and flexible conductive strips (e.g., thin in the X-direction), or flexible wires, that are disposed at desired intervals in the X-direction along the length of the extended length photovoltaic module assembly. In other words, in some embodiments, the connection regions $170A_A$, $170B_A$ and interconnection regions $170A_B$, $170B_B$ do not extend the complete length L of the photovoltaic module assembly in the X-direction, and thus include discrete connections that are spaced apart along the continuous length L of the current carrying regions $170A_C$, $170B_C$. In this case, the connection regions $170A_A$, $170B_A$ and/or interconnection regions $170A_B$, $170B_B$ of the larger cross-section busbars 170A', 170B' may have a length that is between about 100 µm to about 3 centimeters (cm) in the X-direction. In other configurations, the connection regions $170A_A$, $170B_A$ and/or interconnection regions $170A_B$, $170B_8$ may have a length that is substantially equal to the length of a sub-module in the X-direction. The connection regions $170A_A$, $170B_A$ may have a width in the Y-direction (FIG. 3D) that is from about 100 µm to about 3 cm. The connection regions $170A_A$, $170B_A$ and/or interconnection regions $170A_B$, $170B_B$ may have a thickness in the Z-direction and Y-direction, respectively, from about 0.01 mm to about 2 mm, such as from about 0.1 mm to about 0.2 mm. The current carrying regions $170A_C$, $170B_C$ may have a length that is substantially equal to the length L of the photovoltaic module in the X-direction and a width in the Y-direction (FIG. 3D) that is from about 4 mm to about 40 mm. Furthermore, the current carrying regions $170A_C$, $170B_C$ can have a thickness in the Z-direction from about 0.01 mm to about 2 mm, such as from about 0.025 mm to about 0.5 mm, such as from about 0.1 mm to about 0.2 mm.

Interconnection and Rework Process Examples

As briefly discussed above, in some cases one or more of the photovoltaic modules 110 in a photovoltaic module assembly may become damaged during the photovoltaic module assembly manufacturing process, during storage or transportation, or after being placed in normal operation for a period of time. The presence of a damaged photovoltaic module can render the complete photovoltaic module assembly useless for its intended purpose. If a photovoltaic module becomes inoperable in a conventional photovoltaic module assembly it would cause the complete conventional photovoltaic module assembly to be scrapped, thus creating a significant scrap cost and significant amount of waste due to need to also throwaway functioning photovoltaic modules and other useful components. Therefore, there is a need for the photovoltaic module assembly described herein, which can be reworked to make it functional again.

In one example, a photovoltaic module assembly 400A, as shown in FIG. 4A, includes five photovoltaic modules 110A-110E and one of the photovoltaic modules, such as photovoltaic module 110C, is not functioning properly and thus needs to be removed from the photovoltaic module assembly 400A. The process of removing the problematic photovoltaic module 110C from the photovoltaic module assembly 400A may include the following steps.

First, as shown in FIG. 4B, the damaged photovoltaic module 110C is removed from the photovoltaic module assembly 400A. In this example, the damaged photovoltaic module 110C is removed by sectioning or cutting through the various layers and components within the photovoltaic module assembly in the space found within the interconnection regions 310B and 310C, which are formed on either side of the damaged photovoltaic module 110C. In configurations where the photovoltaic module assembly includes one or more of the flexible photovoltaic module assembly components, such as a flexible front sheet 151 and flexible back sheet 109, the sectioning process may be easily performed by use of a blade, scissors, shears, a cut-off saw or other similar cutting device. The process of removing the damaged photovoltaic module 110C can be completed such that the multiple busbars 170, such as busbars 170A and 170B, are at least partially exposed in the remaining portions of the photovoltaic module assembly 400A. In some configurations, the cut formed during the sectioning process is made outside of a module edge seal (not shown). The module edge seal is separately disposed around the edges of each photovoltaic module 110 (e.g., module edge seal is disposed in the X-Y plane) and between the front sheet 151 and back sheet 109 within the photovoltaic module assembly. The module edge seal may be formed from the same material as the edge seal 310 described above.

Next, as shown in FIG. 4C, once the damaged photovoltaic module 110C has been removed the remaining portions of the photovoltaic module assembly 400A can be joined together to form a functioning reworked photovoltaic module assembly 400B. The region of the reworked photovoltaic module assembly 400B where the remaining portions of the photovoltaic module assembly 400A are connected is referred to herein as a junction 410. The process of forming the junction 410 will typically include electrically connecting (e.g., soldering, tack welding, etc.) the sectioned portions of the busbar 170A, such as busbar section $170A_1$ from the left portion and busbar section $170A_2$ from the right portion, and connecting the sectioned portions of the busbar 170B, such as busbar section $170B_1$ from the left portion and busbar section $170B_2$ from the right portion. The process of joining the remaining portions of the photovoltaic module assembly 400A may also include delivering energy to the various components found at the junction 410, such as the front-side adhesive 101A and the back-side adhesive 101B in both portions of the photovoltaic module assembly 400B, to form an environmental seal at the junction 410.

FIG. 5A illustrates one possible configuration of the remaining portions of the photovoltaic module assembly 400A after the damaged photovoltaic module 110C has been removed. During the process of sectioning or cutting through the interconnection regions 310B and 310C of the photovoltaic module assembly an edge configuration that will allow the remaining portions of the photovoltaic module assembly 400A to be easily connected together is formed. In this case, the left remaining portion 500A of the photovoltaic module assembly 400A contains a "step" configuration in which the busbars $170A_1$ and $170B_1$ are both exposed and supported vertically (i.e., Z-direction) by back-side adhesive 101B, and the right remaining portion 500B of the photovoltaic module assembly 400A contains an "inverted step" configuration in which the busbars $170A_2$ and $170B_2$ are both exposed and supported vertically by the front-side adhesive 101A. The process of forming the edge configurations shown in FIG. 5A may be completed by removing the unwanted layers from each end configuration. For example, the "step" configuration formed in the left remaining portion 500A may be formed by removing a portion of the front-side adhesive 101A and front sheet 151 by use of blade, saw or other form of cutting tool.

FIG. 5B illustrates one example of a junction 410 that has been formed using the step and inverted step configuration shown in FIG. 5A. In this example, the step and inverted step configurations found in the left remaining portion 500A and the right remaining portion 500B, respectively, are positioned to overlap each other to form an electrical connection between the exposed portions of the busbars 170. For example, the busbar section $170A_1$ and busbar section $170A_2$ are electrically connected together, and the busbar section $170B_1$ and busbar section $170B_2$ are electrically connected together by use of a conductive adhesive, or are soldered or welded together. In some embodiments, a sealing material 510 may be disposed over both of the edges of the left remaining portion 500A and the right remaining portion 500B of the junction 410 to prevent environmental attack of the components found within the formed reworked photovoltaic module assembly. In some configurations, it is desirable to dispense or position the sealing material 510 such that it is disposed over both of the edges of the left remaining portion 500A and the right remaining portion 500B and also into a gap formed between the opposing walls of the left remaining portion 500A and the right remaining portion 500B in the junction 410 region. In one configuration, the sealing material 510 is dispensed such that it will not interfere with the busbar connections (e.g., electrical connections formed between busbar section $170A_1$ and busbar section $170A_2$ and the busbar section $170B_1$ and busbar section 170B$_2$), but is in contact with at least a portion of each of the opposing walls found in the junction 410 region. The sealing material 510 may include the same materials used to form the edge seal(s) 301, which are discussed above. The sealing material 510 may include a sealing component and/or an adhesive component that are formed from two separate materials. In one embodiment, the sealing component includes a dispensable material that is useful as a barrier to prevent the diffusion of environmental contaminants into the photovoltaic module assembly, and the adhesive component includes a dispensable material that is useful for bonding portions of the junction 410 together.

In some embodiments, at least a portion of the junction 410, such as a region on a non-sunny side of the photovoltaic module assembly, is additionally supported by the placement of a section of a supporting material (e.g., section of back sheet material or other similar material) that is bonded across the joint 410 formed in the photovoltaic module assembly. In one example, a piece of back sheet 109 is bonded across the junction 410, such that it covers at least a portion of the left remaining portion 500A and the right remaining portion 500B. In some cases, the additional supporting material is positioned to overlap the sealing material 510.

Figure 5C:
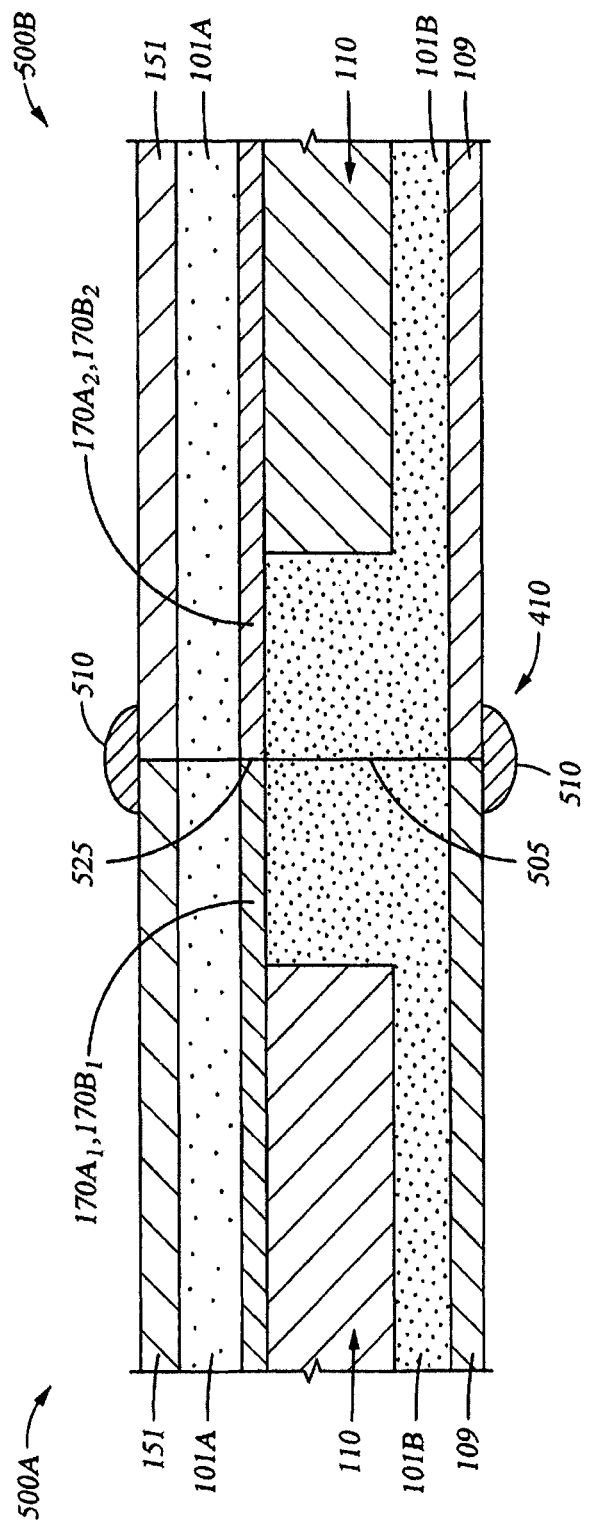
FIG. 5C is a side sectional view of an alternate electrically connected configuration of the two reworked portions of the photovoltaic module assembly, according to an embodiment of the disclosure.

FIG. 5C illustrates another example of a junction 410 that can be formed to interconnect the remaining portions of a photovoltaic module assembly. In this example, the edges of the left remaining portion 500A and the right remaining portion 500B are formed by using a cutting tool that can cut in a vertical direction through the interconnection regions to form the vertical walls 505. In this example, the busbar section 170A$_1$ and busbar section 170A$_2$ are electrically connected together, and the busbar section 170B$_1$ and busbar section 170B$_2$ are electrically connected together when the vertical walls 505 are brought together. In some cases, the busbars 170 may each be electrically connected together at a connection point 525 by use of a conductive adhesive or thermal bonding process. In some embodiments, a sealing material 510 may be disposed over the edges of the left remaining portion 500A and the right remaining portion 500B of the junction 410 to prevent environmental attack of the components found within the formed reworked photovoltaic module assembly. As noted above, in one configuration, the sealing material 510 is dispensed such that it will not interfere with the busbar connections, but is positioned such that the sealing material 510 is in contact with at least a portion of each of the vertical walls 505 found in the junction 410 region.

While FIGS. 4A-4C and 5A-5C illustrate a process of removing a damaged photovoltaic module and forming a new photovoltaic module assembly that has fewer photovoltaic modules than the original photovoltaic module assembly, this process is not intended to be limiting as to the scope of the disclosure provided herein, since the process of removing the problematic photovoltaic module may alternately include replacing the problematic photovoltaic module 110C with a new undamaged photovoltaic module (not shown). In this case, two junctions 410 are formed on either side of the new undamaged photovoltaic module 110 to connect the remaining portions of the photovoltaic module assembly 400A and the new undamaged photovoltaic module 110 together. Therefore, the length of the photovoltaic module assembly 400A need not change from its original size and the power output from the reformed photovoltaic module assembly need not change from its original designed configuration. One will note that it is also generally desirable to replace the damaged photovoltaic module with a new photovoltaic module that has the same performance characteristics (e.g., conversion efficiency (CE), series resistance ($R_s$), fill factor (FF), etc.) to assure that the newly formed photovoltaic module assembly has desirable performance characteristics.

One will appreciate that one or more of the end configurations discussed above in conjunction with FIGS. 5A-5C can also be used to interconnect two photovoltaic module assemblies to form a series connected array of photovoltaic module assemblies. In one example, the left remaining portion 500A shown in FIG. 5A may be the end 103 of a first photovoltaic module assembly and the right remaining portion 500B may be the end 102 of a second photovoltaic module assembly, so that the first and second photovoltaic module assemblies can be easily connected together by joining the ends 102 and 103 of the first and second photovoltaic module assemblies, as similarly shown in FIG. 5B. In some embodiments, a sealing material (e.g., sealing material 510) may be disposed over the ends 102 and 103 of the series connected first and second photovoltaic module assemblies to prevent environmental attack of the photovoltaic modules and other electrical components found within both of the photovoltaic module assemblies.

While the foregoing is directed to embodiments of the present disclosure, other and further embodiments of the disclosure may be devised without departing from the basic scope thereof, and the scope thereof is determined by the claims that follow.

What is claimed is:

1. A photovoltaic module assembly, comprising:
   a front sheet;
   a back sheet;
   an array of photovoltaic modules disposed between the front sheet and the back sheet, each of the photovoltaic modules are separated from one another by a first length, wherein
      each photovoltaic module comprises two or more sub-modules that each have a cathode region and an anode region, and wherein the anode region is disposed at an opposite end of the photovoltaic module from the cathode region,
      adjacent sub-modules within each photovoltaic module are separated by a second length, and
      the first length is greater than the second length;
   a first busbar that is aligned in a first direction, and is electrically coupled to the cathode region of each sub-module; and
   a second busbar that is aligned in the first direction, and is electrically coupled to the anode region of each sub-module.

2. The photovoltaic module assembly of claim 1, wherein each of the photovoltaic modules further comprise:
   a flexible substrate; and
   the two or more sub-modules each comprise a plurality of thin-film layers that are disposed on the flexible substrate.

3. The photovoltaic module assembly of claim 2, wherein the front sheet and the flexible substrate comprise a polymer, and the back sheet comprises a flexible material.

4. The photovoltaic module assembly of claim 3, further comprising:
   a third layer disposed between the back sheet and the photovoltaic module, wherein the third layer comprises a polymer; and
   a fourth layer disposed between the front sheet and the photovoltaic module, wherein the fourth layer comprises a polymer.

5. The photovoltaic module assembly of claim 1, wherein:
the two or more sub-modules each include an array of photovoltaic cells, and
the array of photovoltaic cells extends in a second direction from the cathode region to the anode region, the second direction substantially perpendicular to the first direction.

6. The photovoltaic module assembly of claim 1, further comprising a junction box disposed at a first end of the array of photovoltaic modules.

7. A photovoltaic module assembly, comprising:
a front sheet;
a back sheet;
an array of photovoltaic modules disposed between the front sheet and the back sheet, each of the photovoltaic modules are separated from one another by a first length, wherein
each photovoltaic module comprises two or more sub-modules that each have a cathode region and an anode region, wherein
adjacent sub-modules within each photovoltaic module are separated by a second length,
the first length is greater than the second length, and
the anode region is disposed at an opposite end of the photovoltaic module from the cathode region, each sub-module comprising:
an array of photovoltaic cells extending in a second direction from the cathode region to the anode region, each of the photovoltaic cells separated from one another by a third length, wherein the third length is smaller than the second length;
a first busbar that is aligned in a first direction, and is electrically coupled to the cathode region of each sub-module; and
a second busbar that is aligned in the first direction, and is electrically coupled to the anode region of each sub-module.

8. The photovoltaic module assembly of claim 7, wherein the photovoltaic modules each further comprise:
a flexible substrate; and
the two or more sub-modules each comprise a plurality of thin-film layers that are disposed on the flexible substrate.

9. The photovoltaic module assembly of claim 8, wherein the front sheet and the flexible substrate comprise a polymer, and the back sheet comprises a flexible material.

10. The photovoltaic module assembly of claim 9, further comprising:
a third layer disposed between the back sheet and the photovoltaic module, wherein the third layer comprises a polymer; and
a fourth layer disposed between the front sheet and the photovoltaic module, wherein the fourth layer comprises a polymer.

11. The photovoltaic module assembly of claim 7, wherein:
the two or more sub-modules each include an array of photovoltaic cells, and
the array of photovoltaic cells extends in a second direction from the cathode region to the anode region, the second direction substantially perpendicular to the first direction.

12. The photovoltaic module assembly of claim 7, further comprising a junction box disposed at a first end of the array of photovoltaic modules.

13. A photovoltaic module assembly, comprising:
a front sheet having a first end and a second end, which is opposite to the first end;
a back sheet having a first end and a second end, which is opposite to the first end;
an array of photovoltaic modules disposed between the front sheet and the back sheet, wherein
the array of photovoltaic modules are positioned in a first direction between the first end of the front sheet and the back sheet and the second end of the front sheet and the back sheet,
a gap is formed in the first direction between adjacent edges of adjacent photovoltaic modules disposed within the array,
an edge of a first photovoltaic module of the array of photovoltaic modules, disposed closest to the first end of the front sheet and the back sheet, is positioned a first end length from the first end of the front sheet and the back sheet,
the first end length is larger than the gap, and
each photovoltaic module comprises two or more sub-modules that each have a cathode region and an anode region, and wherein the anode region is disposed at an opposite end of the photovoltaic module from the cathode region;
a first busbar that is aligned in the first direction, and is electrically coupled to the cathode region of each sub-module; and
a second busbar that is aligned in the first direction, and is electrically coupled to the anode region of each sub-module.

14. The photovoltaic module assembly of claim 13, wherein each of the photovoltaic modules further comprise:
a flexible substrate, and
two or more sub-modules that comprise a plurality of thin-film layers that are disposed on the flexible substrate.

15. The photovoltaic module assembly of claim 14, wherein the front sheet and the flexible substrate comprise a polymer, and the back sheet comprises a flexible material.

16. The photovoltaic module assembly of claim 15, further comprising:
a third layer disposed between the back sheet and the photovoltaic module, wherein the third layer comprises a polymer; and
a fourth layer disposed between the front sheet and the photovoltaic module, wherein the fourth layer comprises a polymer.

17. The photovoltaic module assembly of claim 13, wherein:
the two or more sub-modules each include an array of photovoltaic cells, and
the array of photovoltaic cells extends in a second direction from the cathode region to the anode region, the second direction substantially parallel to the first direction.

18. The photovoltaic module assembly of claim 13, further comprising a junction box disposed at the first end of the front sheet and the back sheet.

19. The photovoltaic module assembly of claim 13, wherein at least one of the photovoltaic modules is configured to be removed from the photovoltaic module assembly.

20. The photovoltaic module assembly of claim 13, wherein the first and second busbar each comprise a plurality of conductive strips.

* * * * *